(12) United States Patent
Schultz

(10) Patent No.: US 10,716,879 B2
(45) Date of Patent: Jul. 21, 2020

(54) SMOKE EVACUATOR AND EVACUATION SYSTEM

(71) Applicant: Nascent Surgical, LLC, Eden Prairie, MN (US)

(72) Inventor: Leonard S. Schultz, Bloomington, MN (US)

(73) Assignee: Nascent Surgical, LLC, Eden Prairie, MN (US)

(*) Notice: Subject to any disclaimer, the term of this patent is extended or adjusted under 35 U.S.C. 154(b) by 413 days.

(21) Appl. No.: 15/830,970

(22) Filed: Dec. 4, 2017

(65) Prior Publication Data

US 2018/0085502 A1 Mar. 29, 2018

Related U.S. Application Data

(63) Continuation of application No. 13/972,332, filed on Aug. 21, 2013, now Pat. No. 9,833,549.

(60) Provisional application No. 61/692,128, filed on Aug. 22, 2012, provisional application No. 61/740,263, filed on Dec. 20, 2012.

(51) Int. Cl.
| | |
|---|---|
| *A61M 1/00* | (2006.01) |
| *A61B 46/00* | (2016.01) |
| *A61B 46/23* | (2016.01) |
| *A61M 37/00* | (2006.01) |
| *A61M 31/00* | (2006.01) |
| *A61B 17/20* | (2006.01) |
| *A61B 46/20* | (2016.01) |

(52) U.S. Cl.
CPC .............. *A61M 1/00* (2013.01); *A61B 46/00* (2016.02); *A61B 46/23* (2016.02); *A61M 1/0039* (2013.01); *A61B 2046/205* (2016.02); *A61B 2046/236* (2016.02); *A61M 1/0088* (2013.01); *F04C 2270/041* (2013.01)

(58) Field of Classification Search
CPC combination set(s) only.
See application file for complete search history.

(56) References Cited

U.S. PATENT DOCUMENTS

| | | | |
|---|---|---|---|
| 3,604,421 | A | 9/1971 | Pizzella |
| 4,076,099 | A | 2/1978 | Proksch et al. |
| 4,111,753 | A | 9/1978 | Folsom et al. |
| 4,153,055 | A | 5/1979 | Etes et al. |

(Continued)

FOREIGN PATENT DOCUMENTS

| | | |
|---|---|---|
| WO | 8911885 | 12/1989 |
| WO | 9316741 A1 | 9/1993 |

(Continued)

OTHER PUBLICATIONS

European Office Action for European Application No. 13756781.4, dated Sep. 30, 2019 (7 pages).

(Continued)

*Primary Examiner* — Tatyana Zalukaeva
*Assistant Examiner* — Ilya Y Treyger
(74) *Attorney, Agent, or Firm* — Dorsey & Whitney LLP

(57) ABSTRACT

A smoke evacuator and evacuation system for removing gaseous and/or particulate byproducts of surgical procedures and noxious vapors from chemicals is provided and includes an end effector or vacuum head positionable at a surgical site, the end effector including a plenum, a plenum support for preventing the plenum from collapsing, and an adaptor for coupling the end effector or vacuum head to a vacuum source.

11 Claims, 11 Drawing Sheets

(56) References Cited

U.S. PATENT DOCUMENTS

| | | |
|---|---|---|
| 4,692,140 A | 9/1987 | Olson |
| 4,764,165 A | 8/1988 | Reimels et al. |
| 4,921,492 A | 5/1990 | Schultz et al. |
| 4,969,880 A | 11/1990 | Zamierowski |
| 5,015,243 A | 5/1991 | Schifano |
| 5,192,276 A | 3/1993 | Gatti |
| 5,226,939 A | 7/1993 | Nicolas et al. |
| 5,234,428 A | 8/1993 | Kaufman |
| 5,279,599 A | 1/1994 | Wilk |
| 5,312,296 A | 5/1994 | Aalto et al. |
| 5,320,329 A | 6/1994 | Hoetzl et al. |
| 5,674,219 A | 10/1997 | Monson et al. |
| 5,678,564 A | 10/1997 | Lawrence et al. |
| 5,722,949 A | 3/1998 | Sanese |
| 5,868,722 A | 2/1999 | Yeh et al. |
| 5,941,873 A | 8/1999 | Korenfeld |
| 6,055,987 A | 5/2000 | Griesbach et al. |
| 6,071,267 A | 6/2000 | Zamierowski |
| 6,110,259 A | 8/2000 | Schultz et al. |
| 6,156,004 A | 12/2000 | Tremaine et al. |
| 6,513,529 B1 | 2/2003 | Kamen et al. |
| 6,663,610 B1 | 12/2003 | Thompson et al. |
| 6,942,650 B1 | 9/2005 | Schultz et al. |
| 7,207,977 B2 | 4/2007 | Thompson et al. |
| 9,833,549 B2 | 12/2017 | Schultz |
| 2003/0188851 A1 | 10/2003 | Laird et al. |
| 2004/0049165 A1 | 3/2004 | Thompson et al. |
| 2010/0137775 A1 | 6/2010 | Hu et al. |

FOREIGN PATENT DOCUMENTS

| | | |
|---|---|---|
| WO | 9953833 A1 | 10/1999 |
| WO | 0238033 A9 | 7/2003 |
| WO | 2012145474 A1 | 10/2012 |

OTHER PUBLICATIONS

Nascent Surgical, "SQUAIR Surgical Smoke Capture System—Features and Benefits," Mar. 28, 2011, retrieved on Nov. 28, 2013: URL:http://www.youtube.com/watch?v=nungW-udZP4.

European Office Action for European Application No. 13756781.4, dated Nov. 9, 2016 (7 pages).

International Search Report and Written Opinion of the International Searching Authority for International Patent Application No. PCT/US2013/055976, dated Dec. 5, 2013 (11 pages).

Cornet et al., "Efficacy of Prevention by High-Efficiency Particular Air Filtration or Laminar Airflow Against Aspergillus Airborne Contamination During Hospital Renovation," Infect. Control Hosp. Epidemiol., Jul. 1999, pp. 508-513, vol. 20, No. 7, Abstract (2 pages).

Enggaard et al., "Influence of Local Air Suction on the Density of Air-Borne Bacteria During Cementation of Alloplasties," Ugeskr Laeger, Feb. 10, 1997, pp. 952-955, vol. 159, No. 7, Abstract (1 page).

Friberg, "Ultraclean Laminar Airflow ORs," AORN J, Apr. 1998, pp. 841-842 & 845-851, vol. 67, No. 4, Abstract (1 page).

Friberg et al., "Zoned Vertical Ultraclean Operating Room Ventilation. A Novel Concept Making Long Side Walls Necessary," Acta. Orthop. Scand., Dec. 1996, pp. 578-582, vol. 67, No. 6, Abstract (1 page).

Mangram et al., "Guideline for Prevention of Surgical Site Infection," Special Articles, 1999, pp. 97-118.

Olson et al., "A New Device for Open Surgery Smoke Capture," Nascent Surgical, LLC, pp. 1-18.

Olson, Memo from Particle Calibration Laboratory Manager, Department of Engineering, University of Minnesota, dated Nov. 21, 2011 (3 pages).

Schultz et al., "Unique Devices for Effectively Removing Surgical Plume," Surg. Serv. Management, Apr. 2000, pp. 8-12, vol. 6, No. 4 (3 pages).

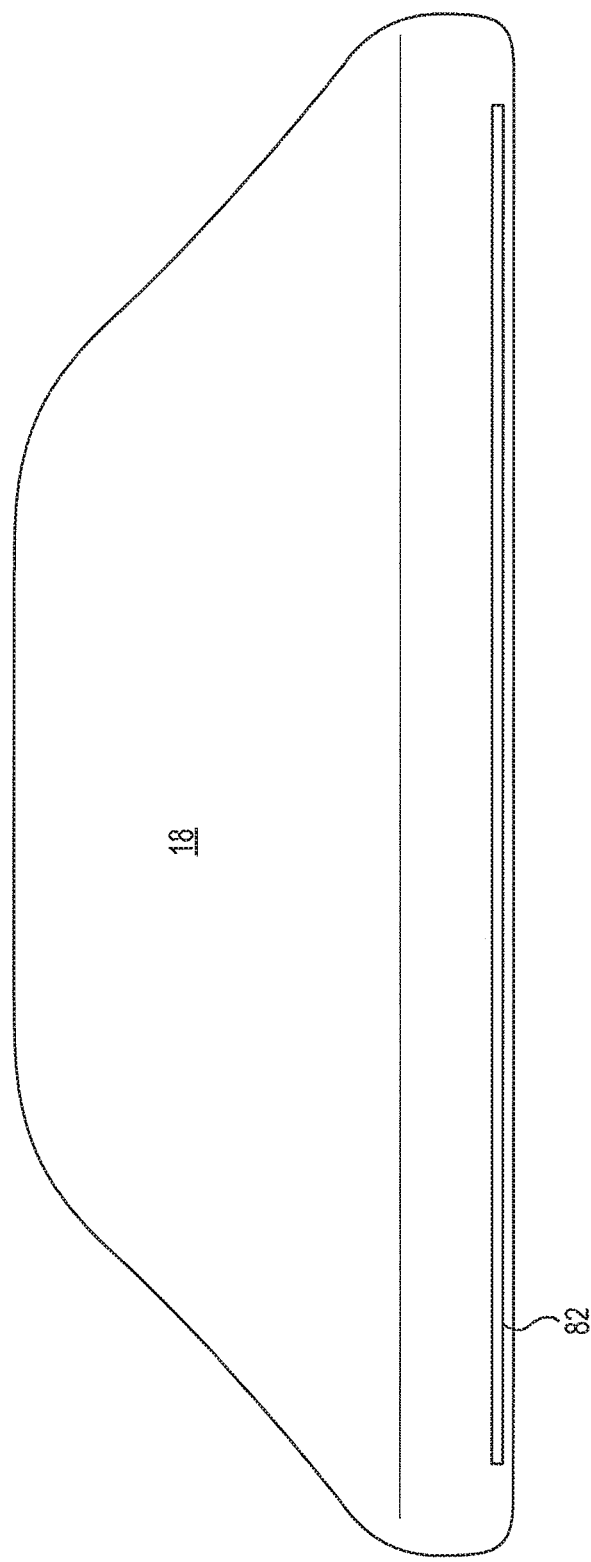

SMOKE EVACUATOR AND EVACUATION SYSTEM

CROSS-REFERENCE TO RELATED APPLICATIONS

This application is a continuation of U.S. patent application Ser. No. 13/972,332 filed Aug. 21, 2013, issued as U.S. Pat. No. 9,833,549 on Dec. 5, 2017, which claims priority to U.S. Provisional Patent Application No. 61/692,128, filed Aug. 22, 2012, and to U.S. Provisional Patent Application No. 61/740,263, filed Dec. 20, 2012, each of which are hereby incorporated by reference in their entirety.

BACKGROUND

This invention relates to equipment, systems and methods for the removal of gaseous and/or substantially gaseous material. Such material includes, but is not limited to aerosol and particle byproducts of surgical procedures and any procedures involving cutting, heating or burning, such as odors from chemicals, ultrasonic vapors, and ion dust particles. More particularly, the present invention relates to an evacuator or vacuum head for an evacuation system that efficiently removes smoke, vapor, or plumes released by chemicals or produced by the use of lasers, sonic cutting and/or cautery or other surgical techniques or instruments at a surgical site.

Heating and/or burning of tissue during surgical procedures have become commonplace. An unwanted byproduct of such heating and/or burning, however, is the smoke generated thereby. Smoke plumes can obscure the surgeon's field of vision and the odor generated is unpleasant and distracting to the entire surgical team and to the patient, if awake. Moreover, the smoke plume may contain infectious agents that present a danger to persons in the operating room, and which can leave a lingering contamination within the operating area. Chemical vapor (e.g., such as that produced by the cleaning of computer parts) is, likewise, irritating to the respiratory tract of those who inhale it and may be carcinogenic.

Smoke evacuation and filtering systems have been developed to remove smoke plumes from surgical sites and chemical vapors from the work environment. Such systems typically include a hose connected to a vacuum source or generator and a suction wand connected to the hose, that is, placed at the site where the aerosol is generated. Various filtration systems have been used in conjunction with such vacuum generators to remove odor and infectious agents. Typically, the wand and hoses of known evacuation and filtration systems have required the constant attention or activity of an attendant to hold the wand or the nozzle of the hose close to the surgical site. Another problem is that the flow of air through the hose nozzle and the suction motor are sources of excessive and unwanted noise in the operating room or at the workstation.

More recently, at least in part to address the problems with wands, smoke evacuation systems may include an end effector that can be held in place at a surgical site without the constant attention of a nurse or other attendant. At least one such evacuation system and end effector is disclosed in U.S. Pat. No. 4,921,492 (Schultz et al.) and U.S. Pat. No. 7,207,977 (Thompson et al.), the disclosures of which patents are incorporated herein by reference. Schultz et al. disclose an end effector for removing the gaseous byproducts of laser surgery from a surgical site. The end effector includes a flexible hose and a pliable vacuum head adhesively attachable in a substantially airtight relationship around a surgical site. The vacuum head includes a generally annular plenum for drawing plumes away from the surgical site from around a 360° arc. A porous plenum support prevents the flexible plenum from collapsing in the presence of a vacuum, and diffuses the vacuum around the entire periphery of the plenum.

U.S. Pat. No. 5,015,243 (Schifano) discloses another smoke evacuator including a flexible suction head for surrounding an operative site to draw smoke and air from around a perimeter of the site as smoke is produced. In one embodiment, the suction head is a doughnut shaped tubular member including a plurality of radial openings on an interior surface of the tubular member that faces the operative site. Schifano teaches that the tubular ring member may be circular or oval, and that it need not completely surround the operative site as long as air is drawn substantially in a surrounding fashion.

While known smoke evacuation systems and end effectors may be well-suited for their intended purposes, it would be advantageous if the end effectors could be selectively varied in size and shape to accommodate different sizes of incisions and different procedures, if end effectors could be made available with the intake opening or openings in selected locations, so a particular end effector could be selected depending on the procedure to be performed, if end effectors could be adapted to reduce noise, if an end effector or vacuum head could be integrated with the widely used customary surgical drapes or drape material, and/or if an end effector or evacuator could be adapted to be placed adjacent to and/or on one side of an operating site and/or incision with an intake side facing the operating site and/or incision.

SUMMARY

The present invention provides an evacuator well-suited for removing, evacuating and/or absorbing smoke, chemical vapors, aerosols, gaseous or generally gaseous material, liquids and/or fluids, including fluids with entrained particles or other material. It is well-suited for use in removing such substances from surgical sites, workstations and manufacturing assemblies or processing sites.

The needs outlined above are in large measure solved by a smoke evacuation system and method, including an evacuator, in accordance with the present invention. The embodiments described herein are designed to efficiently and quietly remove smoke or other aerosols, including smoke or bioaerosols (e.g. a mixture of body fluids, irrigant and gas) generated during surgical procedures, and can be used at a surgical site without constant attention or manipulation by the surgeon or an attendant. They would also remove vapor from the work site.

An improved smoke evacuation system and method for removing gaseous and/or liquid or fluid byproducts of surgical or commercial procedures is provided by the present invention. The smoke evacuation system includes a vacuum head positionable at a surgical or other work site. The vacuum head includes a plenum, and a plenum support or plenum supporting material for preventing the plenum from collapsing when a vacuum or low pressure is established therein, and is adapted to facilitate the use of the system in a variety of surgical procedures at a variety of surgical sites.

In one embodiment, the present invention comprises a vacuum smoke evacuator head for coupling to a vacuum source for withdrawing generally gaseous byproducts, including smoke, fine particulate matter, air and the like, from a surgical or commercial site. The smoke evacuator head is substantially made of a generally pliable or flexible material and defines a plenum. A plenum support or supporting material, medium or substance is carried within the plenum to provide support to the plenum and to prevent the plenum from collapsing when a vacuum or relatively low pressure area is established therein. The smoke evacuator head includes an open intake facing and/or intake openings, and may be positioned adjacent to, at or in a surgical site and coupled to a vacuum source. An adhesive may be carried by the head for maintaining it in a selected position or location relative to the surgical site. In one embodiment, the open intake face may comprise a narrow, elongated open face along one peripheral edge of a side of the head, e.g. an edge of a quadrilateral, e.g. trapezoidal, or triangular head, for being positioned adjacent to a surgical site. The head or end effector may have other shapes, too, e.g. have five side edges.

In some embodiments with an elongated open edge, e.g. a generally triangular embodiment, the other edges, or one of them, or a portion of one or both, may be closed and angled with respect to the open edge to help direct airflow into and through the head. In other embodiments, an internal baffle, baffles or flow-directing and/or controlling structure or structures, e.g. walls, diverters, dividers, etc., may be provided to shape and/or direct airflow into and through the head. Such structures may also help rigidify and/or support the head and/or walls thereof, and may be shaped, e.g. tear-drop shaped, to facilitate or tune an airflow flowing past. The head carries or is attached to a transition adaptor by which it may be coupled to the vacuum source. The adaptor may comprise an internal baffle, baffles or flow-directing and/or controlling structure or structures, e.g. walls, diverters, dividers, etc., suitably shaped to control and/or direct airflow into and through the head. Such structures may also help rigidify and/or support the adaptor. In some embodiments, the adaptor can be joined to the head perpendicularly to head and/or the open edge and, in other embodiments it can be positioned and or connected parallel to the head and/or open edge.

In one embodiment, the smoke evacuator head includes at least one access opening which may be selectively expanded in size. Typically, the access opening may be generally centrally located in the vacuum head, and has an initial peripheral edge which may be moved generally concentrically outwardly by selectively removing one or more removable, generally concentric peripheral portions extending substantially around the opening. Also typically, the opening, whether the initial size or one of the expanded sizes, may be covered or sealed before use by a removable film. See, e.g., U.S. Pat. No. 7,207,977, the disclosure of which is incorporated herein by reference.

In yet another embodiment, the smoke evacuator vacuum head forms a plenum including a substantially open facing portion for being positioned generally adjacent to a smoke or aerosol producing site. In one embodiment, wherein the plenum has a top, outwardly facing wall, is generally annular and includes a generally central access opening, the periphery of the opening being formed by an inner wall, the open facing may be formed in and/or adjacent to the inner wall comprising, for example, a bevel and/or a portion of the top wall. This embodiment is well-suited for use in surgical procedures during which a flap or ridge of skin or tissue may be formed, for example, around or as a result of the incision. Such procedures include plastic surgery procedures and mastectomies, for example, where the vacuum induced in the plenum may tend to pull skin flaps or tissue into it, particularly when the skin flap or tissue is held straight up.

In another embodiment, the evacuation system of the present invention comprises an evacuation hose for detachably connecting a vacuum generator or source and a vacuum head generally surrounding or adjacent to a surgical site. In some embodiments, the vacuum head is substantially made of a generally pliable or flexible material and defines a plenum having a generally central opening. A porous plenum supporting material is carried within the plenum to provide a degree of rigidity to the plenum and to prevent the plenum from collapsing when a vacuum or relatively low pressure area is established therein. The plenum includes an open facing region adjacent to the central opening or along a peripheral edge. An adhesive may be carried by the skin contacting wall of the vacuum head for maintaining the vacuum head in place at a surgical site.

An embodiment and feature of the present invention is the concept of a foam supported channel of selectable cross-sectional area incorporated or integrated with a surgical drape, wherein the channel may be used to convey smoke and/or other aerosol debris away from a surgical site.

Any of the embodiments of the smoke evacuation system or vacuum head described herein may be provided in sterile form and in a color acceptable in an operating room environment.

In some embodiment, an effector may comprise an exit port or adaptor. The exit port may be adapted to increase flow velocities by including an area of decreased cross-sectional area and/or baffles, channels or flow-directing and/or enhancing walls or structures. Such baffles, channels or flow-directing and/or enhancing walls or structures may be located in the plenum as well, and may be shaped to facilitate an airflow, e.g. to provide a coherent, quiet flow. The exit port from which the smoke mixture leaves the smoke evacuator may be coupled to a typical conduit or hose.

Any of the embodiments disclosed herein may be formed by a wall or skin which may be made of the same or similar material as the material of a surgical drape. The skin may or may not be fire retardant or resistant, and any of the embodiments may be preferably composed of bio-compatible material and be capable of disposition as such materials are typically disposed of. In some embodiments, a portion or curtain of drape or drape-like material may be carried by or attached to the bottom or underside of the vacuum head and/or plenum for being tucked into the surgical incision, puncture or wound to cover and/or help protect the tissue around and/or inside the incision, puncture or wound from irritation and/or possible infection.

It should be appreciated that features of any of the embodiments of the present invention may be selectively combined to adapt the smoke evacuator vacuum head for a variety of situations and surgical procedures.

Other features and advantages of the smoke evacuation device and method of the present invention will become more fully apparent and understood with reference to the following description and appended drawings and claims.

BRIEF DESCRIPTION OF THE DRAWINGS

FIGS. 10, 11 and 12 depicts embodiments of an end effector in accordance with the present invention, and how embodiments of the end effector may be coupled to embodiments of an adaptor in accordance with the present invention.

DETAILED DESCRIPTION

The accompanying Figures and this description depict and describe embodiments of the smoke evacuation system and method of the present invention, including the smoke evacuator vacuum head, and features and components thereof. Any reference to "the invention" herein shall not be construed as a generalization, limitation or characterization of any subject matter disclosed herein and shall not be considered to be an element or limitation of any appended claim except if and/or where explicitly recitedor stated. As used herein, the terms "evacuator", "smoke evacuator", "end effector", "vacuum head" and like terms are intended to encompass a structure or structures into which gaseous or generally gaseous or particulate material, such as aerosols, smoke or vapor, may be introduced or be drawn from when the structure is operably coupled to a source of low pressure or vacuum. Such a structure or structures may be placed generally adjacent to a site producing a gaseous or generally gaseous material. As used herein the term surgical field is intended to encompass places where an incision or puncture is to be made in the skin or where other surgical operations or procedures are performed or to be performed. With regard to fastening, mounting, attaching or connecting the components of the present invention to form the device and system as a whole, unless specifically described otherwise, such are intended to encompass conventional fasteners such as machine screws, nut and bolt connectors, machine threaded connectors, snap rings, hose clamps such as screw clamps and the like, rivets, nuts and bolts, toggles, pins and the like. Components may also be connected by adhesives, glues, heat sealing, snap fitting, welding, ultrasonic welding, and friction fitting or deformation, if appropriate. Unless specifically otherwise disclosed or taught, materials for making components of the present invention may be selected from appropriate materials such as metal, metallic alloys, natural and manmade fibers, vinyls, plastics and the like, and appropriate manufacturing or production methods including casting, extruding, molding and machining may be used.

Any references to front and back, right and left, top and bottom and upper and lower are intended for convenience of description, not to limit the present invention or its components to any one positional or spacial orientation.

Figure 1:
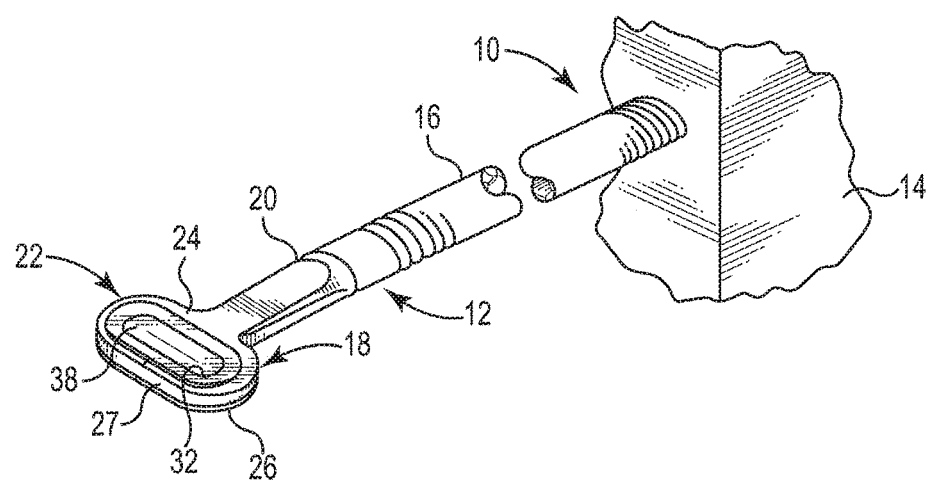
FIG. 1 depicts an embodiment of the present invention.
Figure 2:
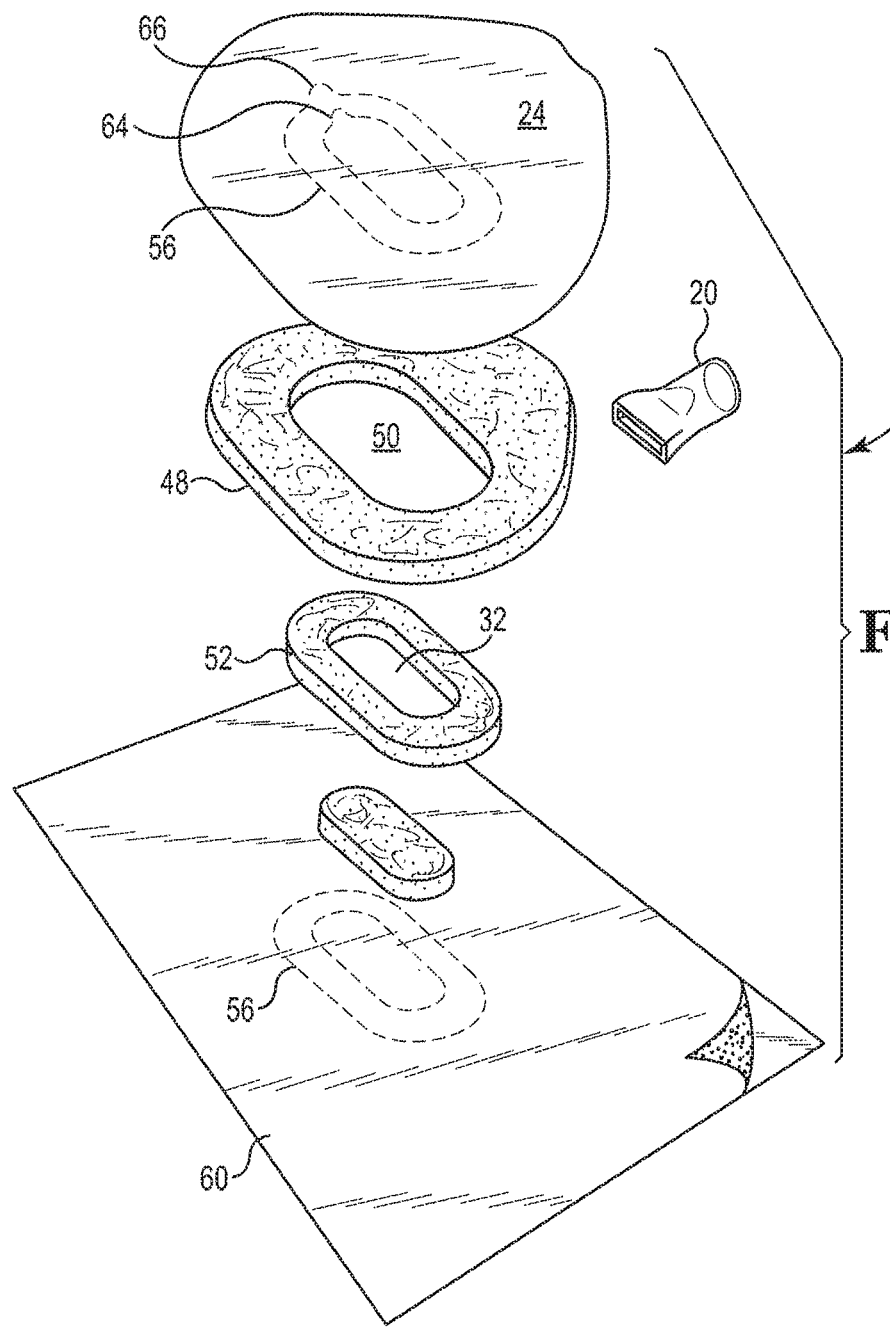
FIG. 2 is an exploded perspective view of an embodiment of the present invention.
Figure 3:
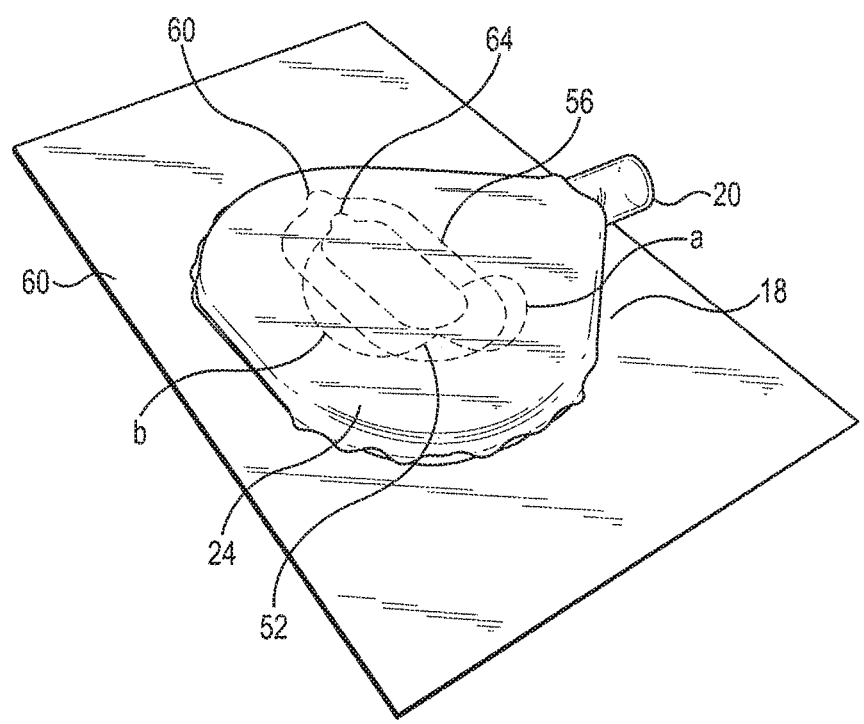
FIG. 3 depicts another embodiment of the invention.

Referring to Figures, including FIGS. 1, 2 and 3, a smoke evacuation system 10 is depicted. The system includes an end effector 12 detachably connected to a suitable vacuum generator and filtration assembly 14. In one embodiment, the end effector 12 may include a flexible hose 16 coupled to a vacuum head 18 by a generally tubular manifold-like handle 20. In one embodiment, the vacuum head 18 includes a generally flat body 22 having a top wall 24, bottom wall 26 and outer sidewall 27 extending between the top wall 24 and bottom wall 26. The body 22 is preferably formed from a nonporous, pliable synthetic resin so that it will conform to the surface surrounding the surgical site. The top, bottom, and side walls 24, 26, 27 together substantially define a generally annular, internal plenum 28. The walls form an outer skin of the plenum 28 and may be composed of a medical grade, pliable, substantially non-porous material. The material of choice may be a synthetic, or it may be a natural material, such as fibrous material, e.g., cellulose or cotton fiber based material, such as presently used in surgical drapes and/or towels. The material of choice may be with or without flame-retardant characteristics. Preferred synthetic materials may be selected from open-celled foams, urethane film, spun lace polyester, nonwoven polyurethane tape and the like.

The top wall 24 includes an access aperture 32, and the bottom wall 26 includes an access aperture 34, typically, but not necessarily, aligned and/or substantially congruent with the top wall access aperture 32. A layer or adhesive may be carried by the top wall 24, and a clear film 38 may be removably carried in place over the top access aperture 32 by the adhesive. The bottom wall 26 may have a first adhesive layer and a clear film removably carried by the first adhesive layer. Another adhesive layer, which may have an antiseptic embedded therein, may be carried by the bottom wall clear film. A sterile, peel-off shield may be removably carried by the antiseptic adhesive layer.

It will be appreciated that, upon application of a vacuum to the body 22, the top and bottom wall 24, 26 would be urged together, thereby reducing the volume of the plenum 28. Therefore, in the end effector 12 depicted in FIGS. 1 and 2, and in other embodiments of the invention described herein, an inner core plenum support 48 formed from a porous material such as foam urethane, or another appropriate reticulated, open-cell foam material, a supporting matrix, or the like, may be carried within plenum 28, to provide the body 22 with some structural rigidity without substantially detracting from the flexibility of the vacuum head 18. The inner core 48 comprises an inner plenum supporting structure 48 that permits the flow of air and smoke into the plenum 28 while blocking the ingress of larger materials such as tissue or surgical materials. The inner core support 48 may be made of a synthetic or natural hydrophobic material to resist absorption of fluids often present in the operative field. A reticulated open cell foam of a size between 5 and 25 pores per inch (ppi) is well-suited for the inner core. In another embodiment, the plenum support core 48 may be molded and/or may be formed contiguously with the outer skin, and may be provided with a plurality or matrix of airflow shafts or channels.

Whether the shape of vacuum head and/or end effector is generally circular, generally oval or a different shape, in some embodiments the end effector 12 provides for evacuation of generally gaseous material substantially around 360°. In other embodiments, see e.g., FIGS. 10, 11 and 12, the vacuum head 18 may have a polygonal shape and a straight, or curved (not shown), open peripheral edge 82, or edges, for being placed adjacent to a surgical site.

Figure 10:
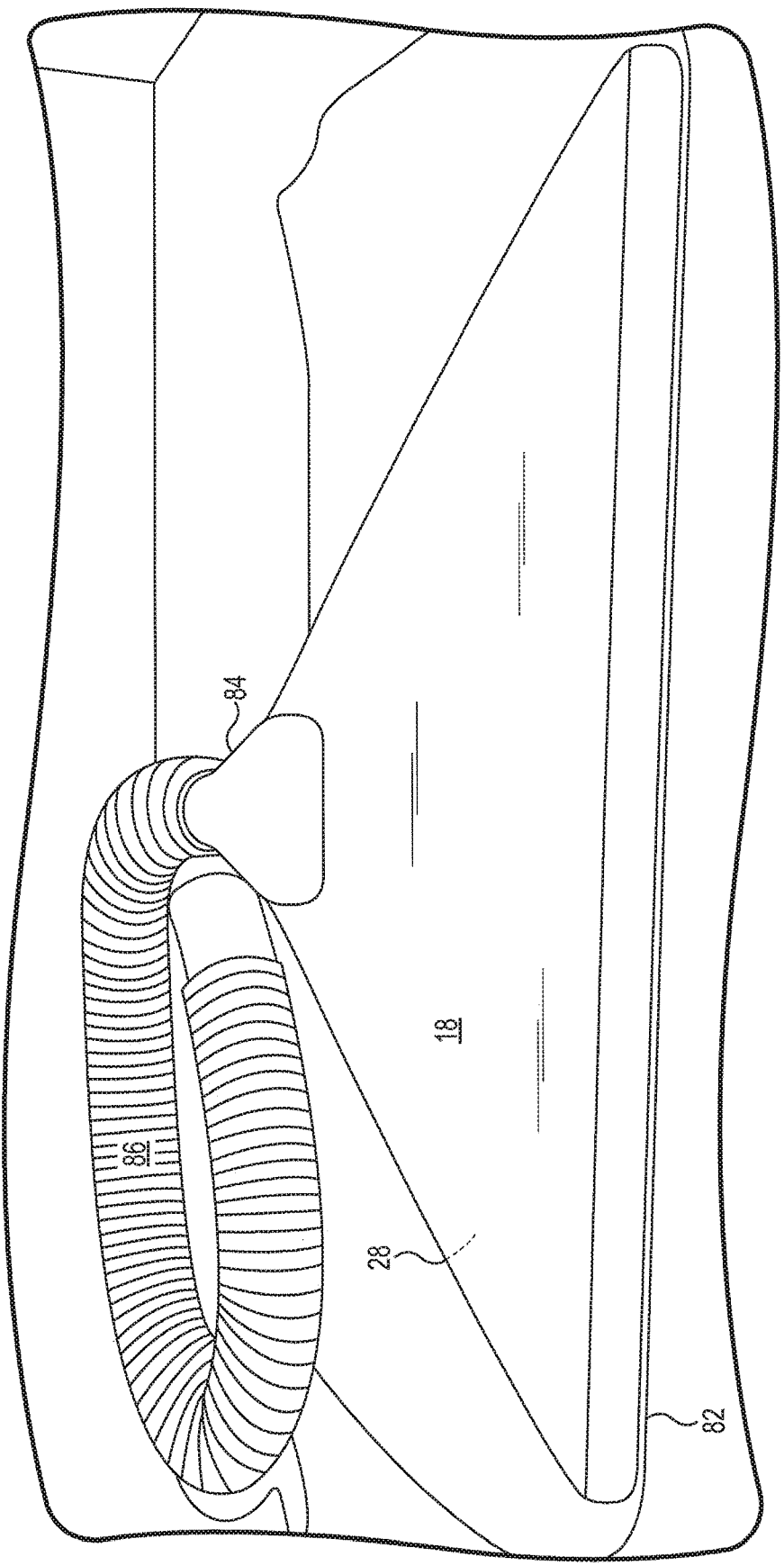
Figure 11:
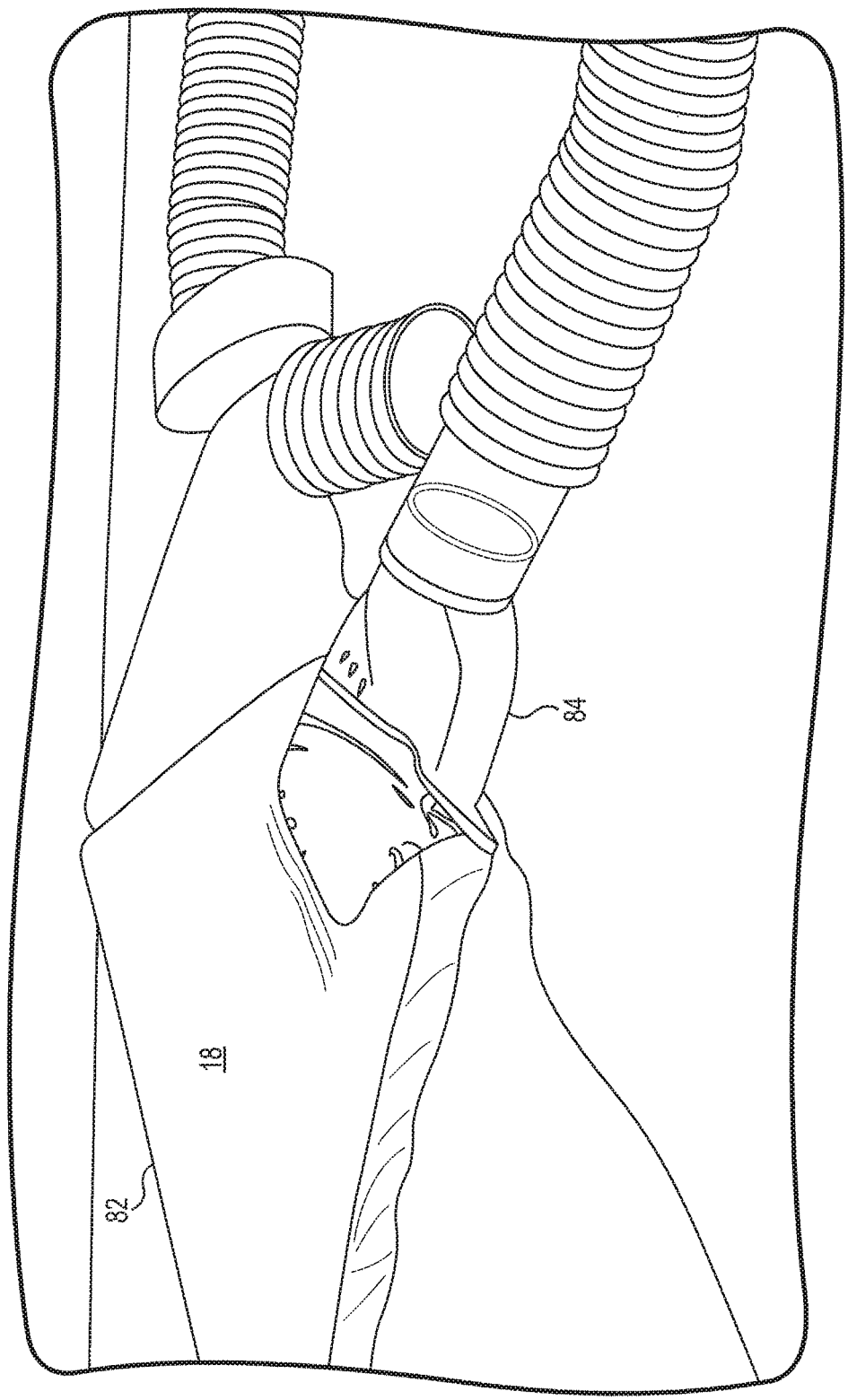

With reference to FIGS. 10, 11 and 12, in some embodiments, the design of the vacuum head 18 and/or plenum 28 is generally triangular which contributes to, helps shape and/or enhances the air flow being directed from an open edge 82 toward an adaptor 84 connecting the plenum to a vacuum tubing 86.

Figure 7:
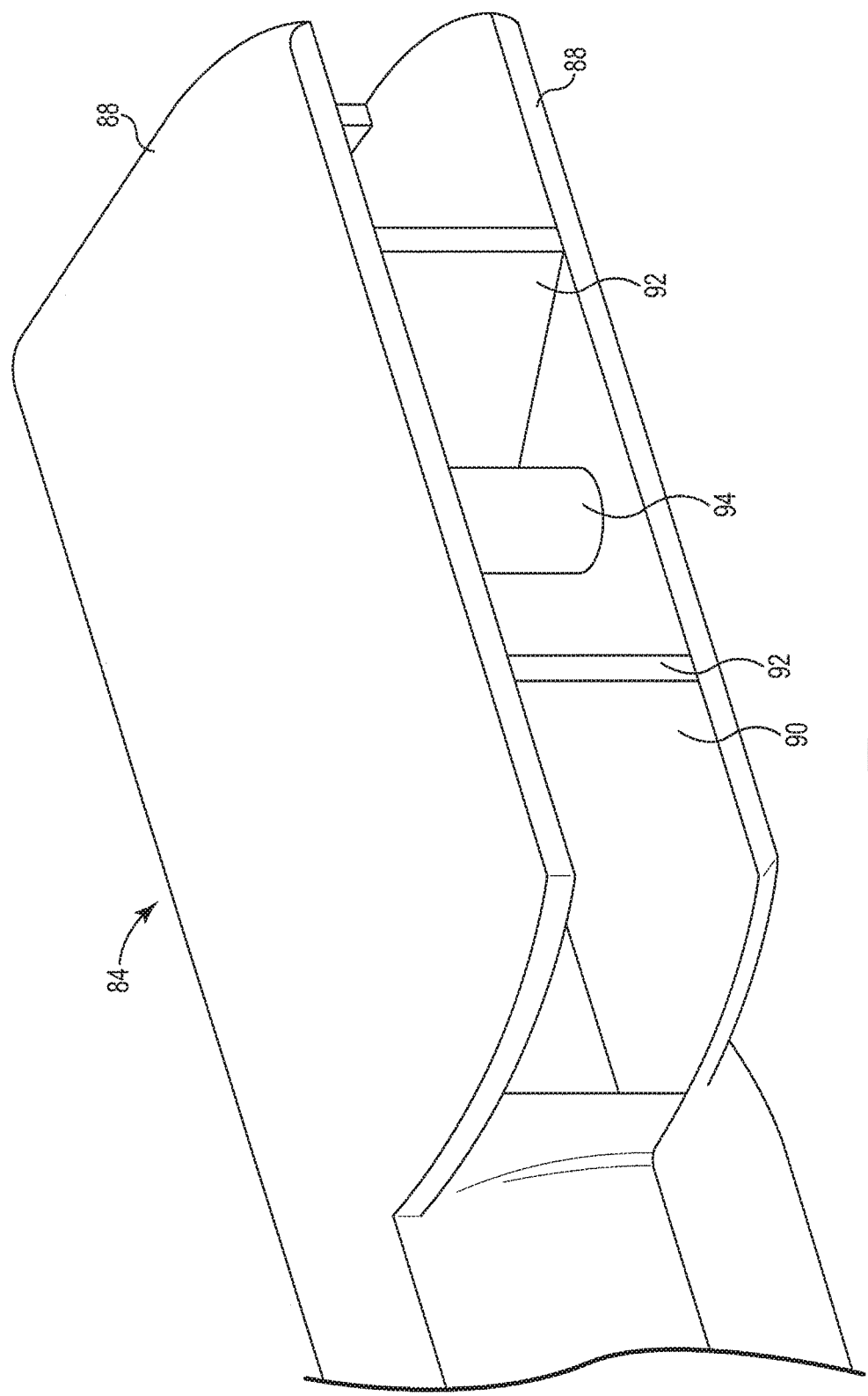
FIG. 7 depicts an embodiment of an adaptor for coupling an end effector to a vacuum source in accordance with the present invention.
Figure 8:
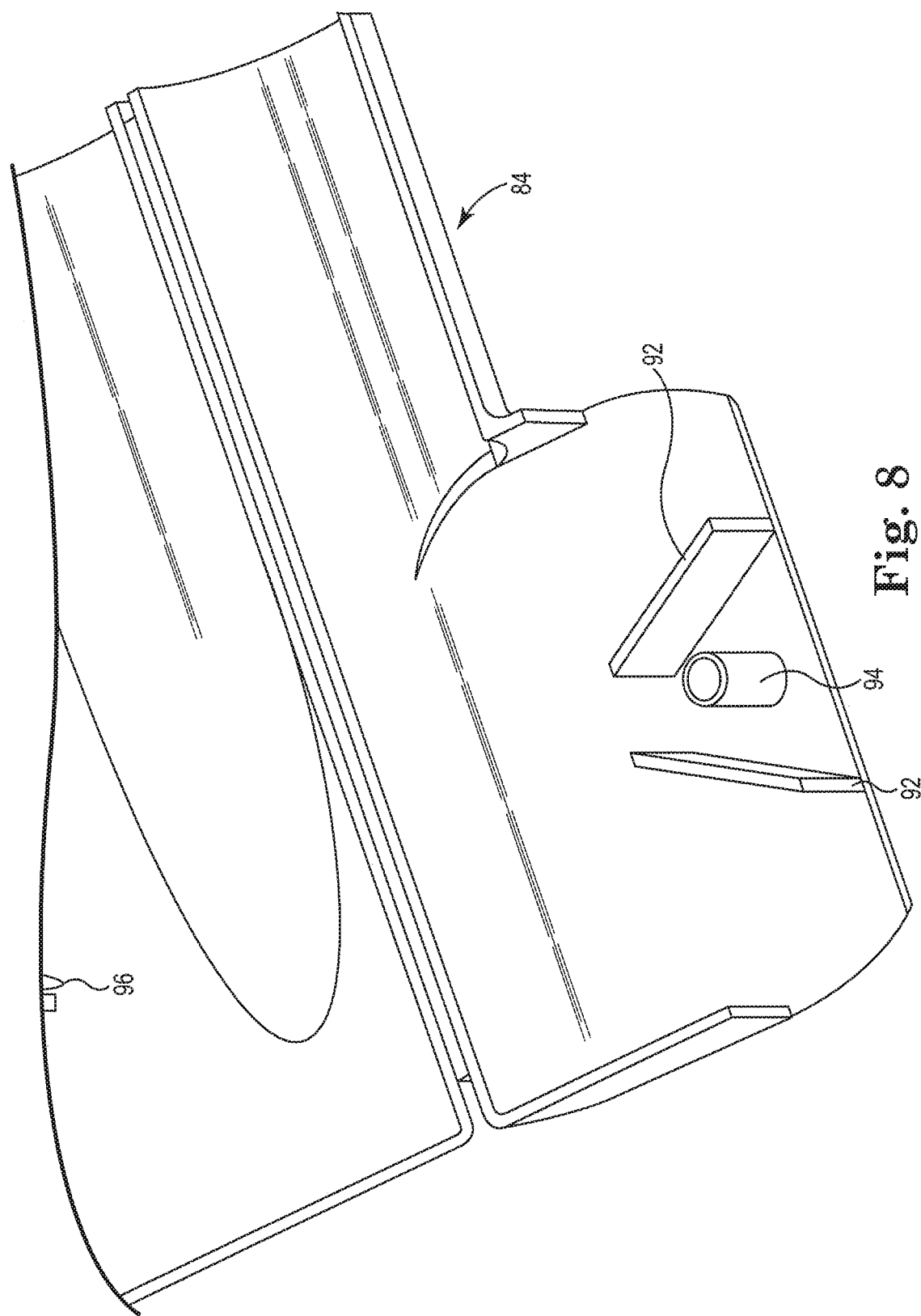
FIG. 8 depicts an embodiment of an adaptor, including embodiments of flow directing and supportive structures.
Figure 9:
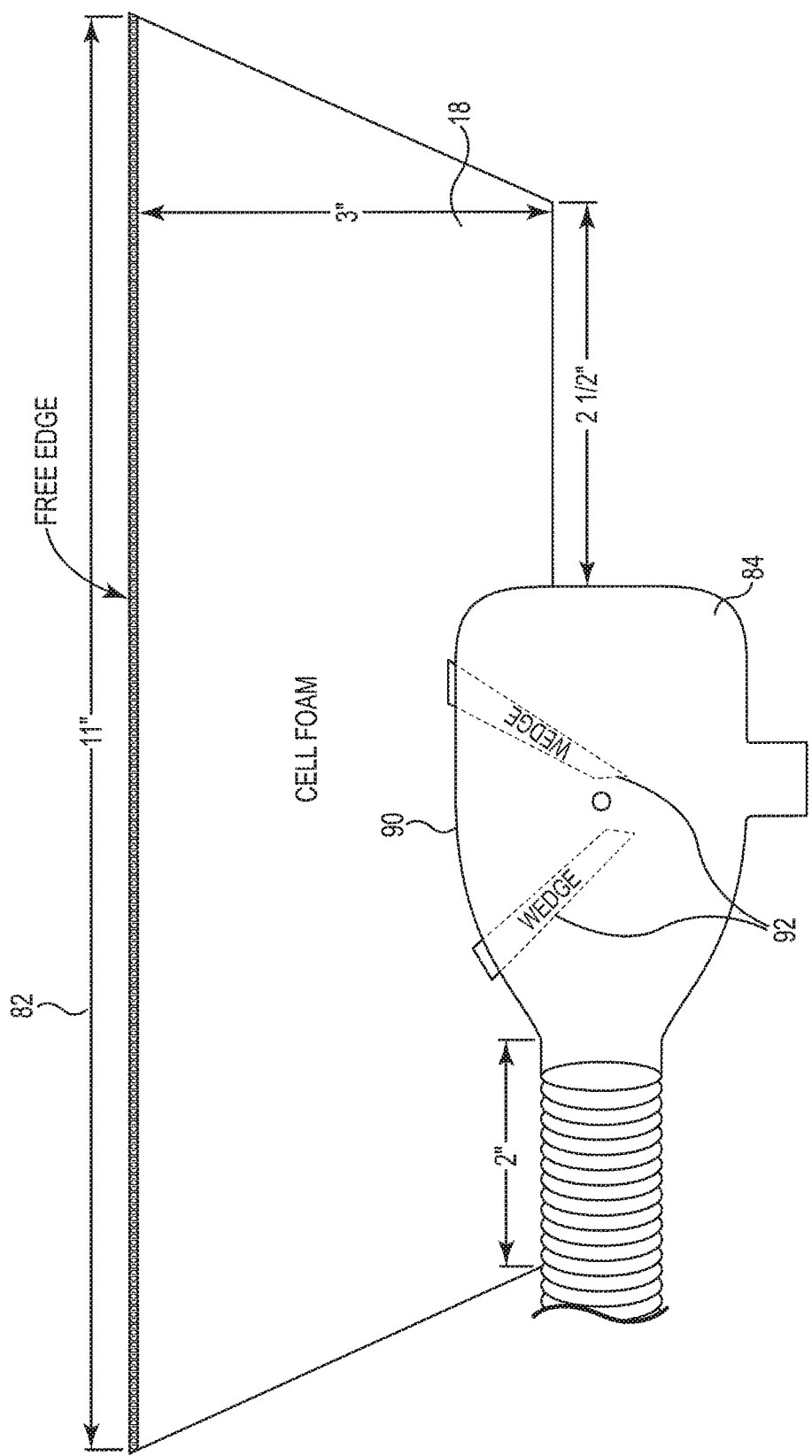
FIG. 9 depicts how an embodiment of the adaptor may be coupled to an embodiment of an end effector.

Referring also to FIGS. 7 and 8, the adaptor 84 has a generally closed body defined by walls 88 and at least one open edge 90 for communication with the plenum 28 of vacuum head 18. FIGS. 7, 8 and 9 also depict an embodiment of the adaptor 84 including airflow directing and/or controlling features, e.g. baffles 92, and/or a post 94 which also may be adapted to cooperate with a lock 96 to form the body of the adaptor 84.

The air flow and/or its direction may create and/or contribute to the level of noise made by the flow (comprising air, smoke and/or particulate matter) as it enters the leading, free, open edge 82 and the cell foam area at the open edge and proceeds to exit the plenum 28 at the adaptor 84. The noise generated may be bothersome to the surgeon and/or other medical staff. Generally, in an operating room environment a noise level of 55 db or less may be preferred, but this level may be varied situationally and/or periodically. In some embodiments, the shape and/or size of the end effector, plenum and/or adaptor may be selected to sonically tune the evacuator and/or the evacuation system, i.e. balance optimal air flow and noise. Another factor or design element which helps balance evacuative flow and noise is based on the distance from the free edge 82 to the point of exit of the air flow from the plenum and/or into the adaptor and/or tubing. For example, in some embodiments, as the distance shrinks or narrows, the noise level increases and may become a distraction. In some embodiments, a distance between 3 and 6 inches may be preferred, but the distance may be varied in accordance with other factors. Another factor influencing and/or affecting airflow and noise is the positioning of the adaptor 84 relative to the free edge 82. In some embodiments, the adaptor 84 can be placed or positioned with its long axis, i.e. along opening 90, parallel to the free edge 82 e.g. see FIG. 9, thereby contributing to a quiet evacuative airflow. The adaptor may be placed and/or oriented otherwise, too, e.g. perpendicularly, see e.g. FIG. 11, and this may influence noise levels produced by the airflow. It should be appreciated the shape, size and location of components and/or their composition and/or flow rates and/or pressure gradients may be selected to sonically tune, optimize and/or balance evacuative flow and noise.

Figure 4:
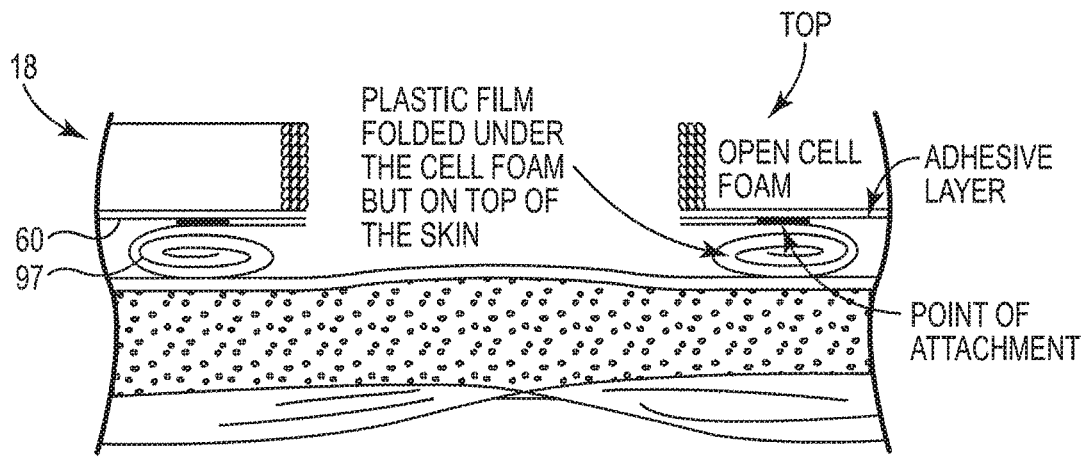
FIGS. 4, 5 and 6 depicts another embodiment of the invention.
Figure 5:
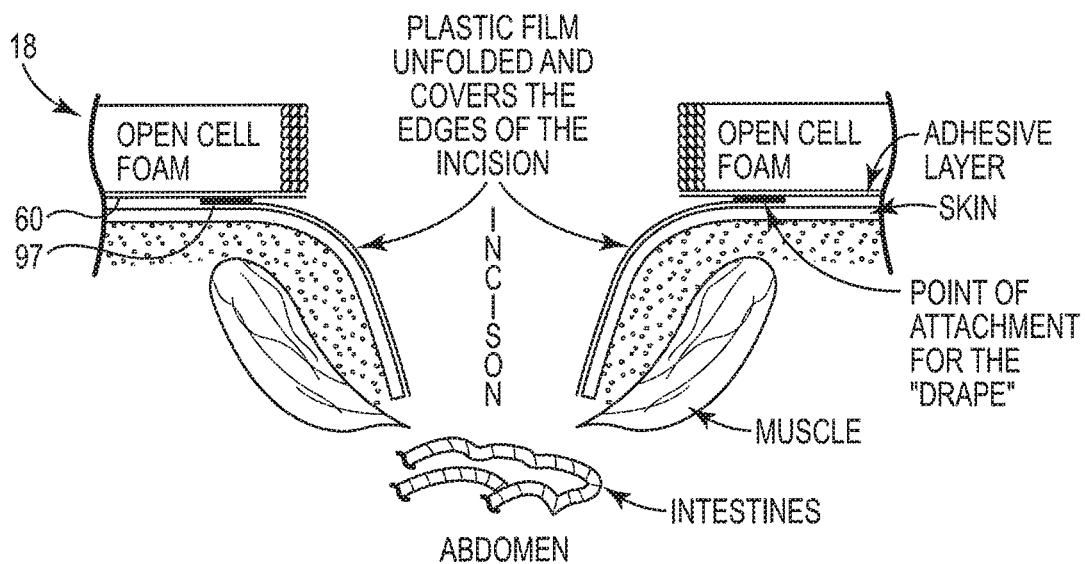
Figure 6:
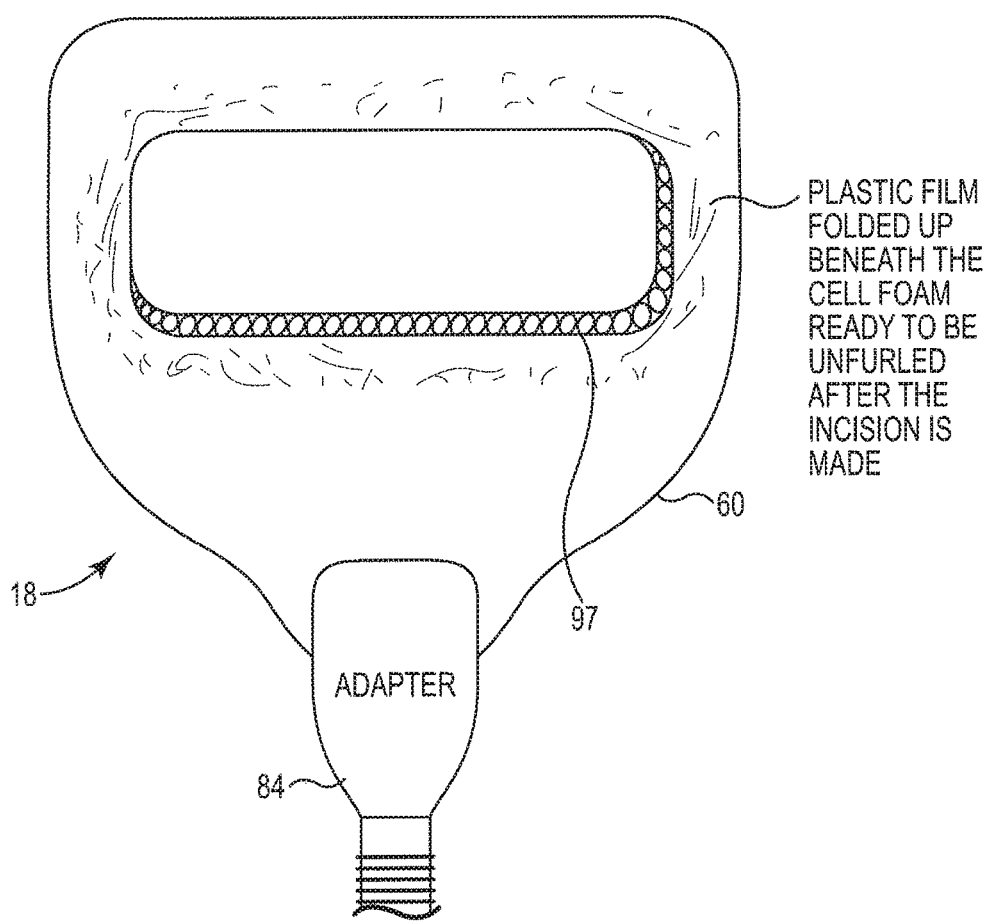

FIGS. 4, 5 and 6 depict another embodiment of the smoke evacuator vacuum head 18 of the present invention, wherein the vacuum head 18 is provided with an access aperture, and is integrated with a surgical drape 60 comprising a relatively large, flexible, generally cloth-like sheet material. Such a drape or drapes are widely used to establish or set off a surgical field, may or may not be generally transparent, and may be formed by a polypropylene material or the like, such as PVC or combinations of polypropylene and cellulose. They may carry an adhesive on one surface for connection to the skin of a patient, typically, four strips of adhesive to define a periphery. One surface of the drape may have an adhesive thereon for attachment to the vacuum head end effector 18. In use, the integrated drape and end effector 18 may be placed over an intended incision site with the access opening aligned with the site. In some embodiments, see e.g. FIGS. 4, 5 and 6, a film, or a portion or roll 97 of drape material or other suitable material may be carried by the underside of the end effector 18 for being tucked into and/or over the incised surface and/or around and/or into an incision, puncture or wound to protect the edges of the incision, puncture or wound from irritation and/or infection.

The use or operation of embodiments of the present invention may be generally similar. The vacuum head, or a drape with the vacuum head integrated, is detachably affixed to the skin surrounding a surgical site by peeling off the sterile peel-off shield and pressing the adhesive layer carried by the bottom wall of the body against the skin. It will be appreciated that the flexible end effector or vacuum head permits a complete, airtight seal of the bottom wall against the skin or any skin covering (such as a clear drape). Films carried by the top and bottom walls can be removed. Upon actuation of the vacuum source, air is drawn into the plenum, and is transported through the adaptor and flexible hose. The porous plenum support carried within plenum prevents collapsing under the influence of the vacuum. The plenum support also may be adapted to enhance the effect of diffusing the vacuum around or through the plenum, thereby enhancing the drawing air into the along the open face or edge. Gaseous or aerosol material produced at the surgical site is thereby drawn into the plenum and evacuated through flexible hose. The plenum support, due to its porous nature, also may act as a filter as the smoke is drawn through it, and/or specific filtration media may be integrated with the end effector.

The end effector(s) and adaptors of the present invention may be formed as single piece and attached to each other, or may be formed as an integral unit. The end effector(s) and/or adaptors of the present invention may be advantageously and hygienically disposed of after a single use, without the necessity of handling contaminated material.

An Appendix comprising eleven (11) pages of a "Draft Final Report" accompany this document. The Appendix relates to smoke capture by embodiments of the present invention, and is incorporated herein by reference in its entirety.

The present invention may be embodied in other specific forms without departing from the essential spirit or attributes thereof. The described embodiments should be considered in all respects as illustrative, not restrictive.

What is claimed is:

1. An evacuation apparatus for removing byproducts, smoke and/or noxious vapors from a surgical site, the apparatus comprising:
    a vacuum head, wherein the vacuum head is sized and shaped for removing byproducts, smoke and/or noxious vapors from a surgical site, the vacuum head comprising:
    a plenum, the plenum having an open peripheral edge shaped as a single straight line;
    a plenum support for preventing the plenum from collapsing when a low pressure is established therein; and
    a transition adaptor configured to couple the vacuum head to a vacuum source via a hose of the evacuation apparatus, the transition adaptor comprising an interior defined by at least one wall arranged perpendicular to the open peripheral edge, wherein the interior of the transition adaptor is for receiving airflow drawn from the plenum, the interior comprising a flow-directing structure for controlling the airflow, the flow-directing structure comprising a baffle, wherein the baffle is spaced apart from the wall.

2. The evacuation apparatus of claim 1, further comprising a surgical drape integrated with the vacuum head.

3. The evacuation apparatus of claim 2, further comprising an adhesive coupled to at least one of the vacuum head or the surgical drape.

4. The evacuation apparatus of claim 2, wherein the surgical drape is partially detachable from the vacuum head and configured to be placed adjacent an incision or tucked into an incision.

5. The evacuation apparatus of claim 1, wherein:
    the transition adaptor comprises an open edge for communication with the plenum of the head; and
    the transition adaptor and the open edge of the transition adaptor have a long axis that is parallel to the open peripheral edge of the vacuum head.

6. The evacuation apparatus of claim 1, wherein the vacuum head has a polygonal shape and the open peripheral edge is straight.

7. The evacuation apparatus of claim 1, wherein the plenum is constructed of a non-porous material.

8. The evacuation apparatus of claim 7, wherein the plenum support is constructed of a porous material.

9. The evacuation apparatus of claim 1, wherein the transition adapter includes an area of decreased cross-sectional area.

10. The evacuation apparatus of claim 1, wherein the baffle is shaped to facilitate a coherent, quiet airflow.

11. The evacuation apparatus of claim 1, wherein the baffle comprises a tear drop shape to facilitate or tune an airflow flowing past the baffle.

* * * * *